United States Patent [19]

Beraha

[11] Patent Number: 4,817,602

[45] Date of Patent: Apr. 4, 1989

[54] VASECTOMY INSTRUMENT

[76] Inventor: Dan Beraha, 912 Woodbriar Ct., Fort Walton Beach, Fla. 32548

[21] Appl. No.: 822,376

[22] Filed: Jan. 27, 1986

Related U.S. Application Data

[62] Division of Ser. No. 643,496, Aug. 23, 1984, Pat. No. 4,682,598.

[51] Int. Cl.⁴ .................. A61B 17/12; A61B 17/32
[52] U.S. Cl. ...................................... 128/305; 128/325
[58] Field of Search ............... 128/305, 318, 346, 325, 128/326; 604/22

[56] References Cited

U.S. PATENT DOCUMENTS

| 352,245 | 11/1886 | Hullhorst | 128/326 |
| 640,517 | 1/1900 | Acheson | 128/326 |
| 821,183 | 5/1906 | Nettleton | 30/349 |
| 1,854,582 | 4/1932 | Erichsen | 30/349 |
| 3,006,344 | 10/1961 | Vogelfanger | 128/318 |
| 3,155,094 | 11/1964 | Hamilton | 128/326 |
| 3,175,556 | 3/1965 | Wood et al. | 128/326 |
| 3,287,751 | 11/1966 | Hoffman | 128/318 |
| 3,363,628 | 1/1968 | Wood | 128/326 |
| 3,631,258 | 1/1972 | Ersek | 128/346 |
| 4,304,236 | 12/1981 | Conta et al. | 128/325 |
| 4,428,374 | 1/1984 | Auburn | 128/318 |
| 4,487,204 | 12/1984 | Hrouda | 128/326 |
| 4,602,629 | 7/1986 | Sohnirman | 128/305 |

Primary Examiner—Michael H. Thaler
Attorney, Agent, or Firm—MacDonald J. Wiggins

[57] ABSTRACT

A disposable vasectomy instrument is provided having a body portion and an insertable module. The body portion includes a jaw portion having a lower fixed jaw and an upper movable jaw into which the module is inserted. The module includes a cutting block having two spaced apart blades and a pair of ligature clips disposed on either side of the blades. The movable jaw is controlled by the operator to simultaneously move the blades forward and close the ligature clips. The physician isolates the vas deferense, engages it within the ligature clips and adjacent the blades. The movable jaw is operated, cutting out a segment of the vas deferens and closing the ligature clips on each severed end of the vas deferens. A separate module is provided for each vas deferens of the patient.

10 Claims, 4 Drawing Sheets

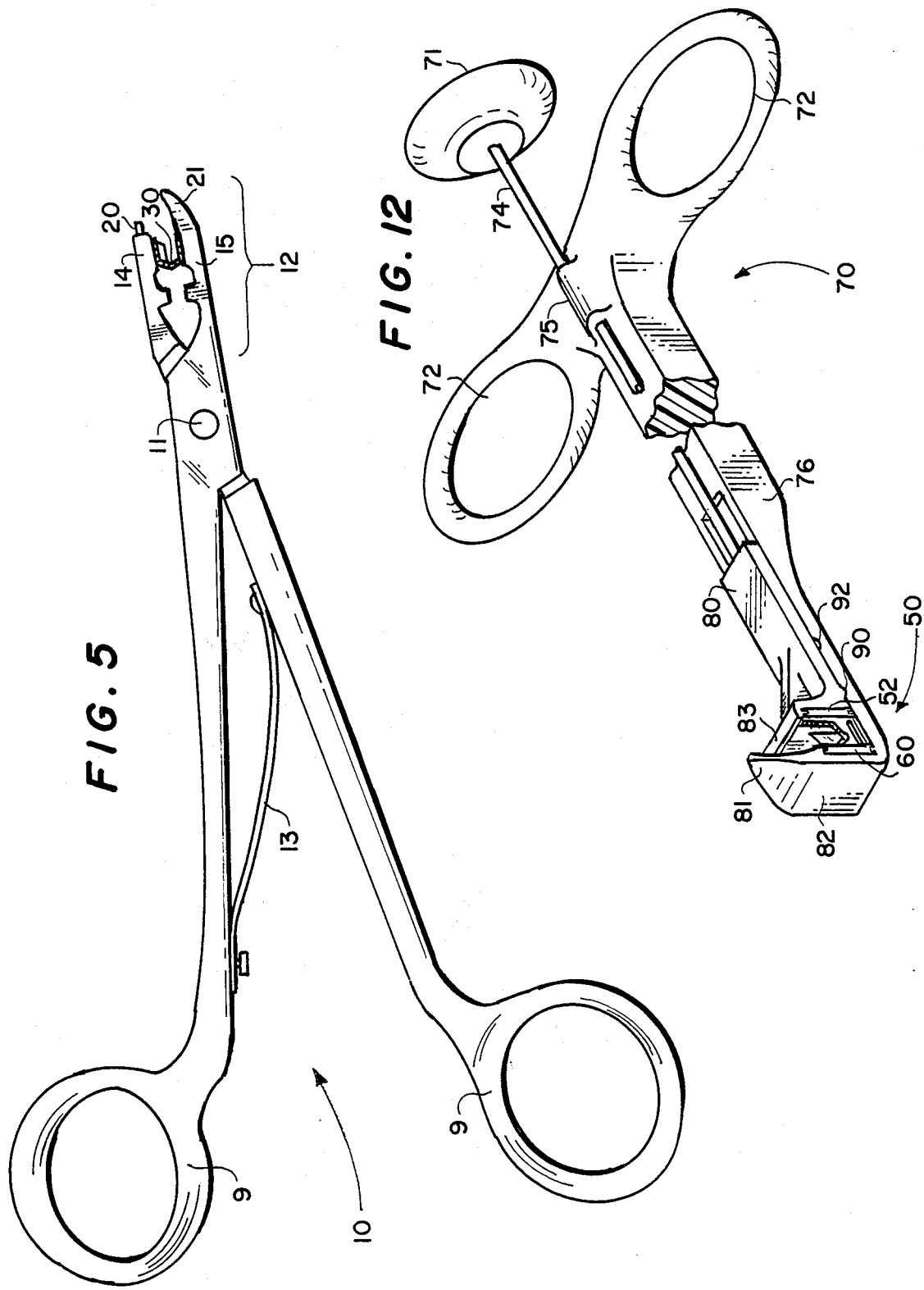

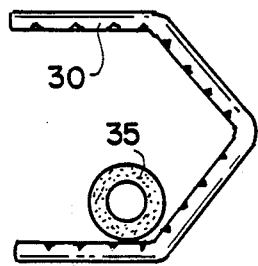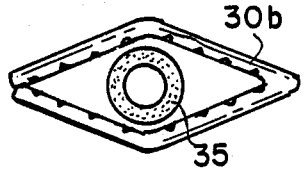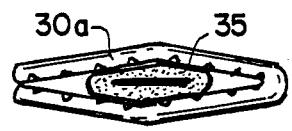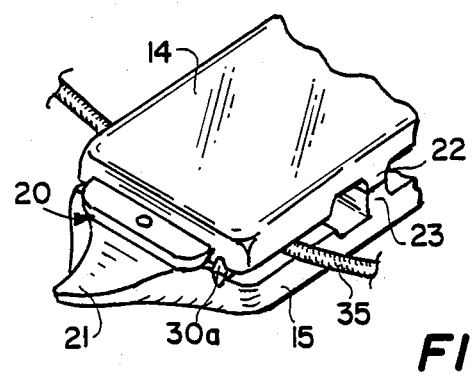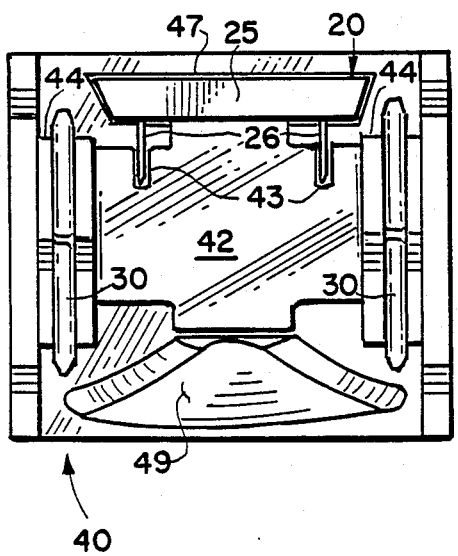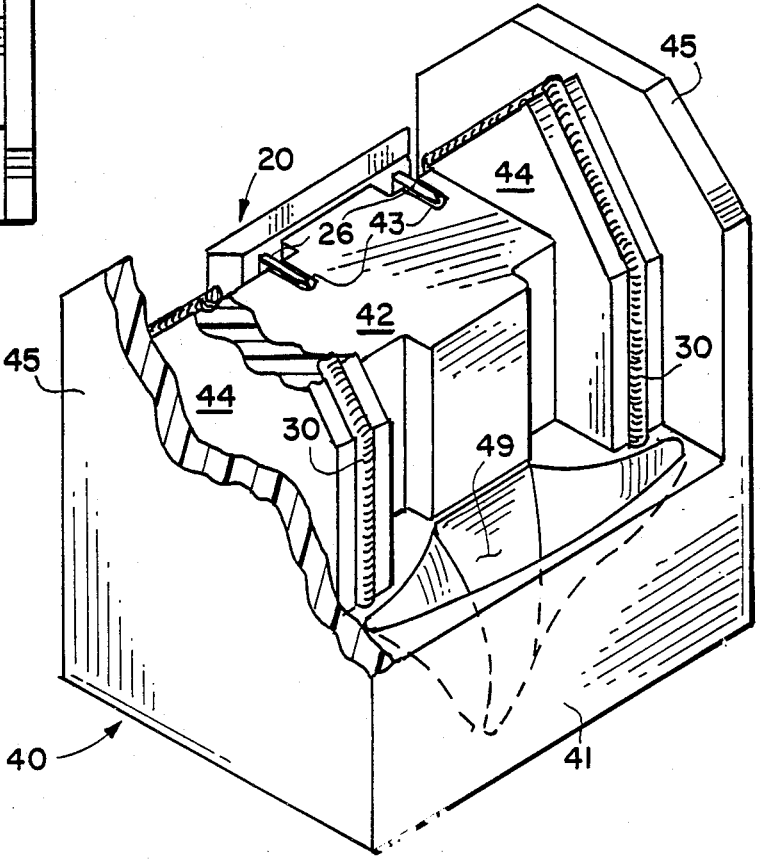

VASECTOMY INSTRUMENT

This is a division of application Ser. No. 643,496 filed 8/23/84, now U.S. Pat. No. 4,682,598.

BACKGROUND OF THE INVENTION

1. Field of the Invention

The present invention relates to an instrument and apparatus for performing vasectomies and more particularly to an instrument which will clamp the vas deferens in two places and simultaneously sever a section of the vas deferens between the clamps

2. Description of the Prior Art

The use of the vasectomy operation to render a male sterile has become increasingly popular. The operation is generally performed as an office procedure under local anesthetic with the patient awake. Many male patients prefer the operation to be performed with only the surgeon present. The procedure as most commonly performed involves locating the vas deferens in the scrotal sac, and elevating the vas by manipulation to a subcutaneous position. A skin incision is made over the vas and a segment of the vas is isolated from the surrounding tissue. Next a pair of hemostats is applied to the vas and the segment therebetween is excised. The cut margins of the vas are then ligated with a nonabsorbable or an absorbable suture, returned to the sac, and the incision sutured closed.

When the surgeon is working alone, the handling of the several instruments needed is awkward and time consuming. For example, it is difficult to suture the cut margins while holding and positioning a hemostat. This step must be performed twice for each side.

There has been a long felt need for a surgical instrument with which the surgeon could contact the vas, install a pair of ligating clips to the vas, and simultaneously cut the vas between the clips. Thus, the time from making the incision to suturing the incision after the procedure would be greatly shortened Ideally, such instrument or the operative parts thereof should be disposable.

It is known in the art to utilize ligature clips which are installed using special clip applying forceps as shown in U.S. Pat. No. 4,434,795 to Mericle. However, these and known similar instruments apply one clip at a time. A pair of clips or cuffs joined by a filament of body implantable material is taught by Bliss in U.S. Pat. No. 3,766,926 for use in performing a vasectomy for the purpose of holding the severed ends of the vas deferens in a spaced relationship such that a reversal of the vasectomy operation could be performed at a later date. Bliss does not teach any specific instrument for applying his prosthesis. Brodsky et al disclose a vasectomy procedure and instrument in U.S. Pat. No. 3,716,056 which assists the surgeon in lifting the vas from the underneath side and out of the scrotum of the patient. However, no provision is made for closing the ends of the severed vas in the Brodsky instrument.

Instruments are known for clamping and cutting an umbilical cord For example, Mattler in U.S. Pat. No. 4,026,294 shows a device for clamping and then cutting an umbilical cord in separate and distinct clamping and cutting steps. However, this instrument is bulky and unsuited for use in performing the vasectomy procedure. Another similar instrument is shown in U.S. Pat. No. 2,524,337 to Whittaker. Whittaker shows a single blade cutter having a scissors like structure with holding clips disposed on either side of the cutter jaws. These clips are adapted to hold a pair of serrated clamps which are temporarily attached to the umbilical cord and the scissors like structure utilized to cut the cord. Neither the size nor the design of the Whittaker device is suitable for use in a vasectomy procedure.

SUMMARY OF THE INVENTION

The present invention comprises a forceps like instrument having a pair of opposing jaws having a width on the order of 1 to 2.5 cm. The upper jaw includes a centralized, longitudinal aperture and a ligature clip-holding groove on either side of the aperture. Opposing the upper jaw is a lower jaw having a cutter receiver surface including a pair of longitudinal parallel slots. On either side of the receiver surface is a groove for holding a clip aligned with the grooves in the upper jaw. Projecting from the receiving surface is a smooth, hook-like guide. A pair of lateral stop surfaces is provided to the rear of the upper and lower jaws to restrain closing of the jaws to a preselected distance. As will be understood, the jaws are operated by a pair of spring loaded handles, preferably having a finger hole in each handle. The spring biases the jaws open. The instrument is preferable made from stainless steel or other suitable metal.

The aperture in the upper jaw of the instrument is adapted to receive a disposable rectangular cutting block. The cutting block includes a base portion which may be formed from plastic which snugly fits the jaw aperture and has a pair of thin cutting blades mounted at right angles to the block surface and spaced apart about 1 cm. In use, the block is inserted in the upper jaw aperture such that the two cutting blades oppose the slots in the lower jaw receiver surface. A ligature clip is installed in each of the two sets of grooves along the outer edges of the jaws. The clips are required to be implantable and may be formed from stainless steel, titanium or the like. A suitable clip is the Hemoclip ® available from Ethicon. Similar clips are available from Weck. Alternatively, clips formed from absorbable material are suitable.

To install the clips and the cutting block, the invention includes a jig which is supplied in a sterile package containing forms for holding a pair of clips in the exact spacing required by the instrument. Between the clips, a block is provided which holds the cutter block assembly. A recess in the base of the jig is shaped to confirm to the hook-like guide of the instrument To load the clips and the cutter block into the jaws of the instrument, the open jaws are placed over the jig and moved downward such that the cutter block slides into the upper jaw slot, the lower jaw guide enters the recess in the jig and the two clips slide into the grooves in the upper and lower jaws. The instrument is withdrawn from the jig and is then ready for use.

After the instrument is loaded, the surgeon makes the required incision in the scrotal sac, picks up the vas deferens with the hooked guide of the lower jaw of the instrument, causing the vas to slide into the clips as it lays across the receiving block. When the vas is in the proper position, the surgeon closes the jaws causing the clips to close and clamp the vas and the cutter blades to cut out a 1 to 2.5 cm section of the vas. As will be understood, this procedure can be performed very smoothly and quickly. The jaw stops permit a desired degree of closure of the clips on the vas without crushing the walls thereof.

The instrument is then removed and opened with the severed section of the vas captured between the two blades which can be removed for pathology. The cutter assembly is discarded and the instrument may be reloaded for the other side.

BRIEF DESCRIPTION OF THE DRAWINGS

FIG. 5 is a perspective view of the instrument of FIG. 1;

FIG. 6, FIG. 7, and FIG. 8 show successive steps in clamping a ligature clip on the vas deferens;

FIG. 9 is a view of the jaw portion of the instrument of FIG. 1 with the cutter block installed and closed on a vas deferens;

FIG. 10 is a top view of a jig utilized in installing the cutter block and the clips in the instrument of FIG. 1;

FIG. 11 is a cut-away perspective view of the jig of FIG. 9;

FIG. 12 is a partial perspective view of an alternative disposable embodiment of the invention;

DETAILED DESCRIPTION OF THE PREFERRED EMBODIMENT

Figure 1:
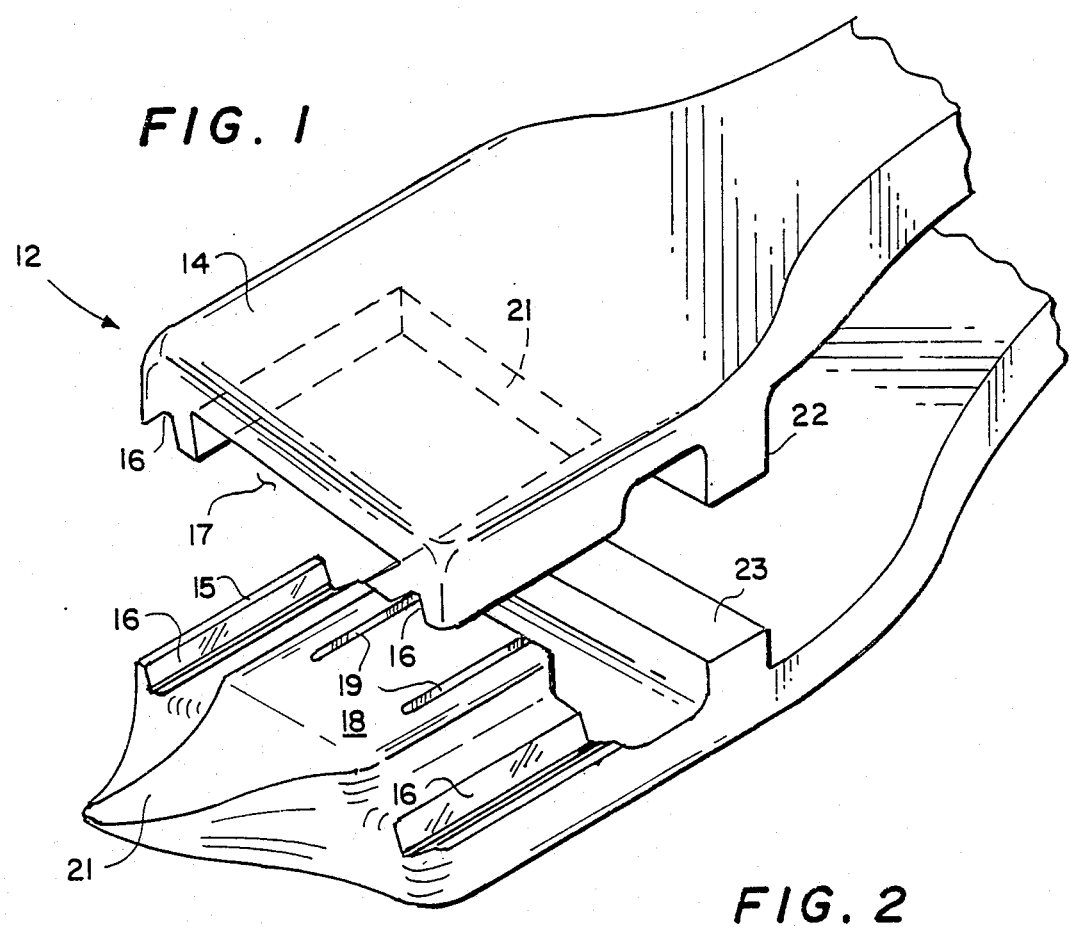
FIG. 1 is a perspective view of the jaw portion of the instrument of the invention.

A first embodiment of the invention utilizes a forceps-like instrument. The operative head portion 12 of the instrument is shown in perspective view in FIG. 1. As will be described below, head portion 12 is designed to receive a disposable insert 20 shown in perspective view in FIG. 2. Head portion 12 includes an upper jaw 14 and a lower opposing jaw 15. Upper jaw 14 includes an aperture 17 for receiving insert 20 and a pair of grooves 16 for receiving a pair of ligature clips. A stop block 22 is provided rearward from the outer end of upper jaw 14.

Lower jaw 15 includes a hook-like guide portion 21 which is preferably somewhat pointed and curved upward at its outer end. As will be discussed below, hook-like guide 21 is of assistance to the surgeon in picking up and introducing the vas deferens into the instrument. To the rear of guide 21 and opposing aperture 17 in upper jaw 14 is a receiver surface 18 having a pair of grooves 19 formed therein. A ligature clip groove 16 is provided on either side of receiver surface 18 and on a plane slightly below the plane of receiver surface 18. A stop block 23 mating with upper jaw stop block 22 is disposed to the rear of lower jaw 15. As will be understood, stop blocks 22 and 23 permit closure of jaws 14 and 15 to a desired degree.

Figure 2:
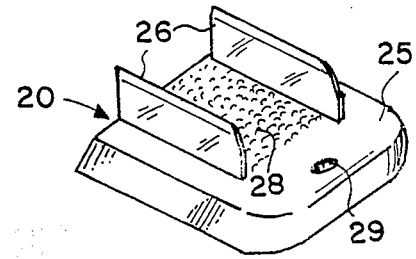
FIG. 2 is a perspective view of a cutter assembly for installation in the jaws of the instrument in FIG. 1.

Disposable insert 20 of FIG. 2 includes a base 25 which may be formed from plastic or other suitable material. The lateral edges of block 25 are tapered to fit the tapered sides of aperture 17 in upper jaw 14 as best seen in the cross-sectional view in FIG. 3 of insert 20 installed in upper jaw 14. A pair of spaced apart thin cutting blades 26 is disposed normal to the surface of block 25. Blades 26 have a sharp cutting surface along the horizontal edges. The forward edges of blades 26 are cut at an angle and rounded to prevent nicking of the vas when entered into the instrument jaws. The length of block 25 is such that when installed in upper jaw 14, the forward edge projects slightly therefrom. A hole 29 in the forward edge of block 25 is provided so that a small hooked tool or the like can be used to quickly withdraw insert 20 for disposal thereof after use. The surface 28 of block 25 between blades 26 is roughened to assist in retaining a severed section of a vas deferens as will be described below.

FIG. 5 is a side view of the complete instrument 10 having jaws 12 with disposable insert 20 installed as well as ligature clips 30. As may be noted, the instrument 10 has conventional handles 9 with a biasing spring 13 which holds the instrument in a normally opened position. Jaws 12 may be closed about pivot point 11 which will close ligature clips 30 and cause blades 26 of insert 20 to seat in grooves 19 and receiver surface 18.

Figure 3:
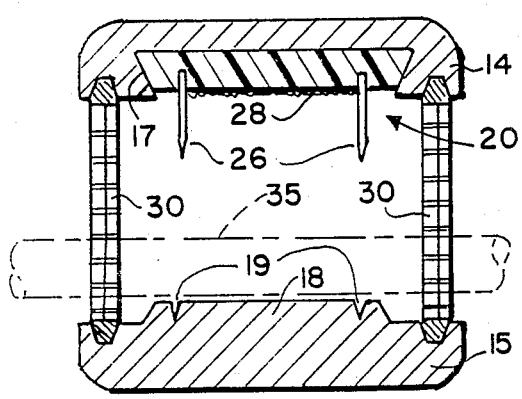
FIG. 3 is a cross-sectional view of the jaws of the instrument having a pair of ligature clips and the cutter block installed therein.
Figure 4:
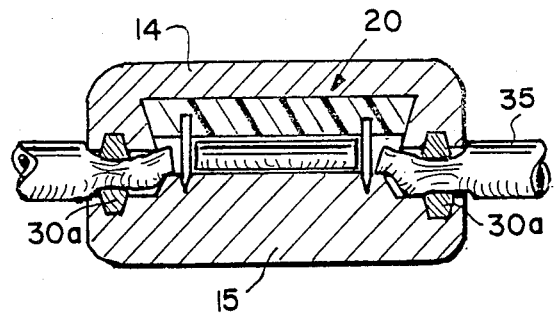
FIG. 4 is a cross-section of the jaw portion of the instrument of the invention in a closed position after cutting a vas deferens.

The vasectomy procedure is performed using the above described action. The action is best explained with reference to FIGS. 3 and 4. In FIG. 3, insert 20 is shown installed in aperture 17 of upper jaw 14 and a pair of ligature clips 30 is installed in grooves 16 in upper and lower jaws 14, 15. To use the instrument, the surgeon performs the necessary incisions to locate and expose the vas deferens. Holding instrument 10, the surgeon inserts hook-like guide 21 under the vas, sliding the vas into the jaws along receiver surface 18 and into ligature clips 30. In FIG. 3, vas 35 is shown as dashed lines in proper position to begin the procedure. The surgeon then quickly closes instrument 10 until stops 22 and 23 contact each other thereby closing clips 30 on the vas and cutting out a section of the vas between clips 30 as shown in FIG. 4. As may be seen, clips 30a have clamped vas 35 on either side of the instrument. Simultaneously, blades 26 have severed a short section of the vas and are seated in grooves 19. At this point, the surgeon may open the instrument releasing the clamped vas ends. The severed section of the vas will be captivated by cutting blades 26 and the friction surface 28 of insert block 25. The surgeon may then remove block 25 from upper jaw 14, remove the vas section for pathology, and dispose of the used insert 20.

Referring now to FIG. 6, 7, and 8, the operation of the ligature clips 30 is indicated. A clip 30 in FIG. 6 is shown with the vas 35 indicated in sectional view in the proper position for closure. In FIG. 7, clip 30 has closed to a shape indicated by 30b. This closure is characteristic of the preferred Hemoclip ® which creates the noted diamond shape as pressure is applied. The stops 22 and 23 are selected such that the complete closure is as shown in FIG. 8 in which the clip condition 30a is closed sufficiently to completely block the lumen of vas 35, yet not to the extent that the tissue is crushed.

A perspective view of the closed jaws 14, 15 of instrument 10 is shown in FIG. 9. As can be noted, stops 22 and 23 are effective to prevent crushing of the vas 35 by clips 30a.

As previously discussed, instrument 10 must be loaded with a disposable insert 20 and a pair of ligature clips 30 prior to each use thereof. It is preferred that these elements be supplied in sterile packaging which is opened just prior to use. Turning to FIGS. 10 and 11, a plastic jig 40 is provided having a pair of ligature clips 30 and a disposable insert 20 installed therein in a portion for loading into instrument 10. The assembly is preferably packaged in a sterile plastic wrap as is well known in the art. In the perspective view of 11, which is partially cut away, it may be noted that jig 40 includes a body portion 41 having a centrally disposed block 42, a pair of end walls 45, and a pair of clip holders 44 between block 42 and walls 45. One vertical surface of block 42 includes a pair of grooves 43 which accept cutting blades 26 of insert 20. As seen in FIG. 10, a recess 47 in base 41 of jig 40 is provided which accepts the forward end of block 25. Recess 47 and slots 43 may be dimensioned to hold insert 20 snugly in place.

An additional recess 49 is provided in the base 41 which is formed to accept hook-like guide 21 of instrument jaw 15.

To load instrument 10, the sterile package containing jig 40, a pair of clips 30, and an insert 20 is opened. The open jaws 12 of instrument 20 are positioned over jig 40 and aperture 17 is guided over the edges of insert 20. The outer edges of jaws 14 and 15 are guided by jig walls 45 such that clips 30 enter slots 16 in response to downward movement of instrument 10, as such movement continues, guide 21 will enter recess 49 and will seat therein. At this point, the clips 30 are in the proper position and insert 20 is fully seated in aperture 17. As shown by the dashed lines in FIG. 1, a stop surface in aperture 17 is provided to ensure full seating of insert 20. Instrument 10 is then withdrawn from jig 40 and is ready for use in the above described procedure.

As will now be recognized, the present invention provides in the above described embodiment an instrument which can be quickly and conveniently loaded with a pair of ligature clips and a cutter assembly. The instrument provides a convenient guide for contacting and positioning the vas deferens, and which permits the surgeon to then simultaneously sever a section of the vas and close the severed ends in one continuous and accurate procedure. Thus, the instrument significantly decreases the time of the procedure compared to the known prior art methods. The operative portions of the instrument, namely the cutting insert and the ligature clips, may be provided in a completely sterile package and inserted in the instrument without handling with the cutting insert being disposable.

ALTERNATIVE EMBODIMENT

Turning now to FIGS. 12 through 15, an alternative embodiment of the invention is disclosed which is fully disposable. Many surgeons prefer an instrument which is supplied in a sterile packaging for one time use. Thus, the need for sterilizing equipment is eliminated. This embodiment comprises two elements as seen in FIG. 12. A body portion 70 formed from a hard plastic or the like and an insertable module 50 are provided. The sterile pack would have one body portion 70 and a pair of the modules 50.

Figure 14:
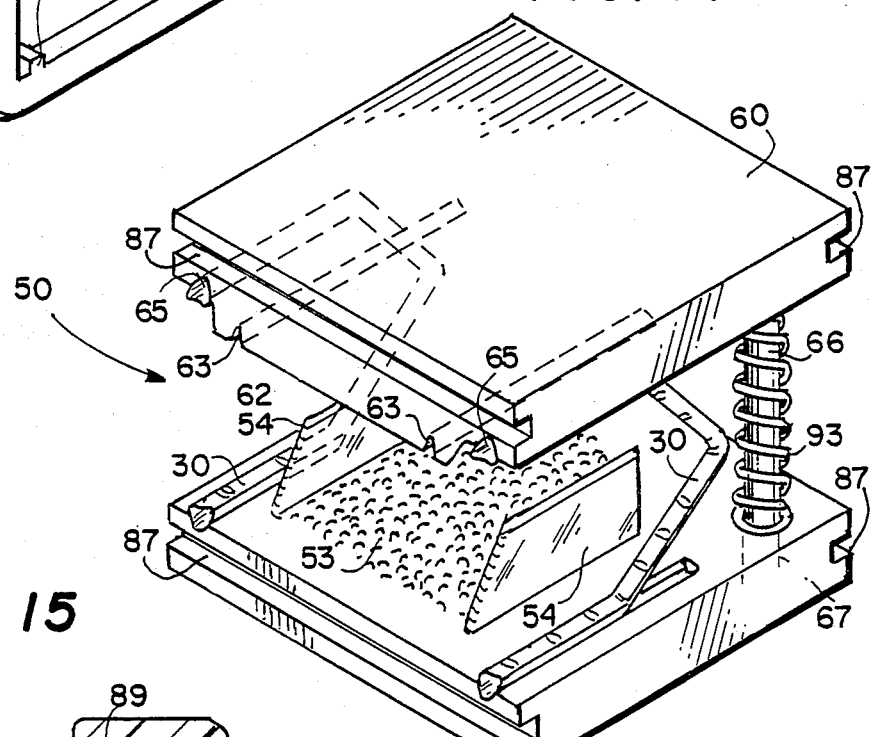
FIG. 14 is a perspective view of the clip and cutting module for insertion in the jaws shown in FIG. 13.

Details of module 50 are shown in FIG. 14. A receiver block 60 is provided having a receiving surface 62 with a pair of slots 63 formed therein. On either side of receiving surface 60 is a groove 65 for receiving one of the ligature clips 30. An opposing cutter block 52 includes matching grooves 65 for ligature clips 30. As will be understood, module 50 is supplied with clips 30 installed in grooves 65. Cutter block 52 includes a pair of cutting blades 54 identical to blades 26 of the first embodiment. The surface 53 between cutting blades 54 is preferably roughened to assist in holding a severed section of the vas. Cutting block 52 is attached to receiver block 60 by means of a pair of pins 66. Pins 66 are anchored in receiver block 60 and project into openings 67 shown as dashed lines in FIG. 14 and is slidable therethrough. Pin 66 and opening 67 include a detent 69 seen in the cross-sectional view of FIG. 15. This detent has sufficient friction to maintain clips 30 in grooves 65. However, the friction may be overcome with a small force tending to push blocks 60 and 52 together as will be described hereinbelow. It will be noted that the lateral edges of blocks 60 and 52 include grooves 87.

Figure 13:
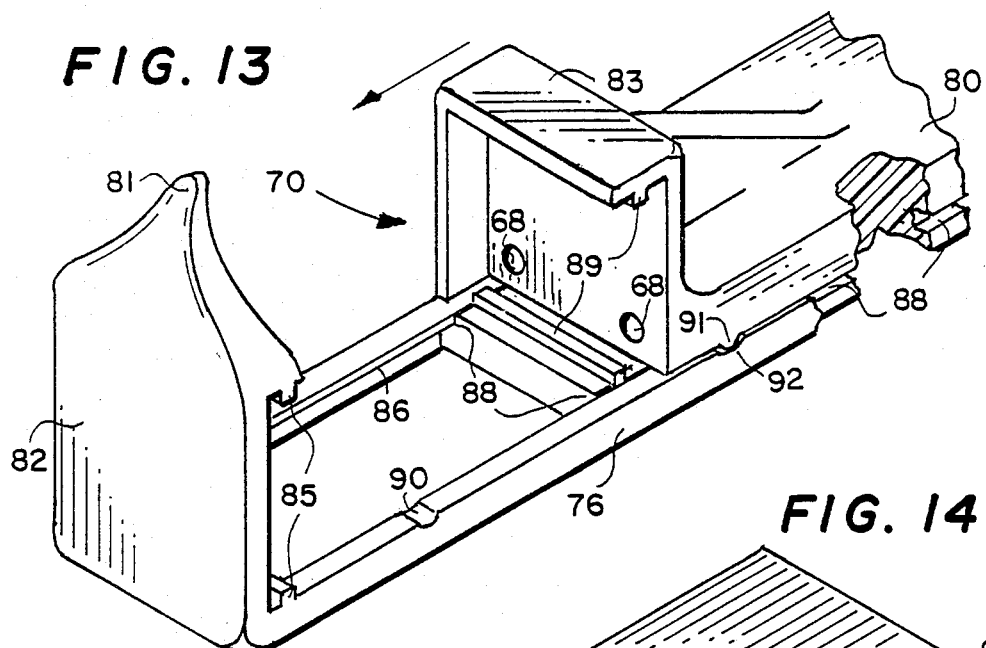
FIG. 13 is a perspective view of the jaw portion of the embodiment of FIG. 12.

A partial view of the jaw portion of instrument body 70 is shown in FIG. 13. Body 70 includes a rail base portion 76, a lower fixed jaw 82, and a movable jaw 83. As shown in the cut away portion, movable jaw 83 includes a base portion 80 having longitudinal grooves 88 therein. Grooves 88 are slidably disposed on rails 86. Thus, movable jaw 83 may move in the direction shown by the arrow toward lower jaw 82. Shallow detent 91,92 defines the initial position for movable jaw 83. Lower jaw 82 includes a hook-like guide 81 which functions in the same manner as guide 21 of the first embodiment. A pair of compression springs 93 biases jaw 83 toward the open position when a module 50 is installed.

Referring to FIG. 12, it may be seen that the body portion 70 includes a pair of finger openings 72, and a guide boss 75 through which a metal rod 74 is slidably disposed. Rod 74 is connected to the base 80 of movable jaw 83 and has a thumb knob 71 attached to the distal end thereof. Knob 71 and rod 74 are used to move jaw 83 along rails 86.

The instrument is supplied with one body portion 70 and a pair of insert modules 50. Initially, jaw 83 is in the initial position in which detent 91 engages detent recess 90. A module 50 is installed in lower jaw 82 and movable jaw 83 as shown in the cross-sectional view of FIG. 15 with keys 85 and 89 engaging grooves 87. Additional details of the sliding jaw may be noted from this figure. A pair of cylindrical recesses 68 is provided in jaw 83 aligned with the two pins 66 of insert 50 to permit forward movement of jaw 83.

As may be recognized, the instrument is ready for use when removed from its sterile packaging. As in the previously described procedure, the surgeon utilizes hook-like guide 61 to contact the vas deferens and guide it into the clips 30 along the receiver surface 62 of receiver block 60 (not shown in the cross-sectional view of FIG. 15). With his fingers in loops 72 of body 70, the surgeon exerts pressure with the thumb on knob 71. When the resistance of detent 69 is overcome, block 52 moves along pins 66 toward receiver block 60, compressing spring 93 and closing ligature clips 30. As complete closure is attained, blades 54 sever the vas in the same manner as described for the first embodiment. As jaw 83 moves toward lower jaw 82, pin 66 enters recess 68. Spring 93 may be selected such that in its completely compressed condition, it acts as a stop as the cutting edges of blades 54 enter slots 63 and clips 30 are closed to the desired extent as previously indicated with reference to FIG. 8.

Figure 15:
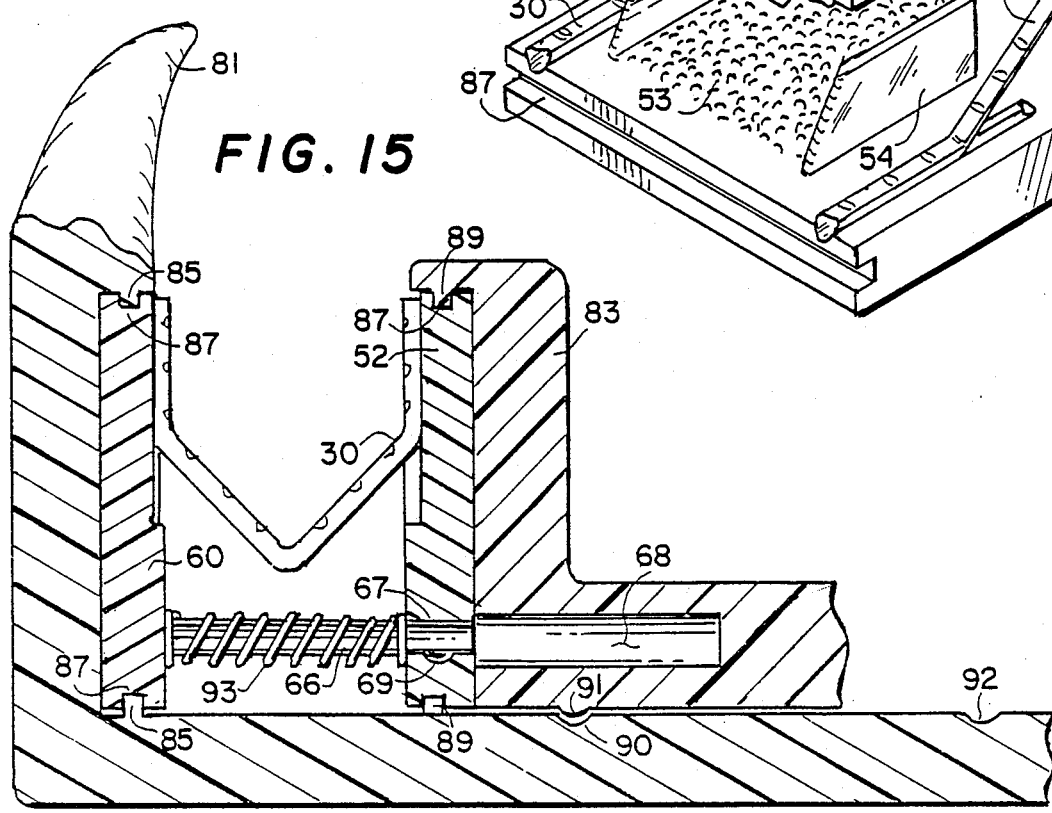
FIG. 15 is a cross-section of the jaws of the embodiment of FIG. 12 having the module of FIG. 14 installed therein.

At this point, the surgeon releases pressure on knob 71 and spring 93 pushes movable jaw 83 back to the original position shown in FIG. 15. This releases the clamped ends of the vas and permits removal of the instrument from the operating field. A small hook-like device may be supplied which can be hooked into opening 67 to assist in removing of block 52. After removal, the severed vas section may be removed for pathology and the block discarded. With the movable jaw 83 is returned to the first detent position with detent 91 engaging detent recess 90, the second module 50 supplied in the package may then be inserted in the jaws and the vasectomy procedure completed. After the second vas is severed and the instrument removed, the severed vas portion can b removed for pathology.

Advantageously, the major portions of this alternative embodiment can be molded from low cost hard plastic at a relatively low cost such that the body portion 70 can be discarded after each proedure.

The specific embodiments of the invention described above are for exemplary purposes and various modifications will be obvious to those of ordinary skill in the art and are considered to fall within the spirit and scope of the invention.

I claim:

1. A disposable surgical instrument for performing a vasectomy comprising:
    an elongate body having a handle at the proximal end thereof and a fixed lower jaw at the distal end thereof;
    a movable jaw slidably disposed on said body, said movable jaw opposing said fixed jaw of said body;
    a rod attached to said movable jaw and projecting beyond said handle of said body, said rod utilized for sliding said movable jaw toward said fixed jaw;
    a replaceable module having a receiver block, said block having a first pair of ligating clip grooves and a planar receiving surface between said first pair of clip grooves, a cutting block having a planar surface opposing said receiving surface and having a second pair of ligating clip grooves aligned with said first pair of clip grooves, a pair of pins attached to said receiver block and extending between said receiver block and said cutting block, said pins frictionally engaging said cutting block, and a pair of open ligating clips disposed in said aligned clip grooves;
    a pair of spaced apart cutting blades having proximal edges attached to said cutting block and sharpened distal edges extending toward said receiver block, said distal edges spaced from said receiving surface; and
    said fixed jaw and said movable jaw including holding means for holding said receiver block and said cutter block therebetween whereby movement of said rod toward said fixed jaw moves said cutter block along said pins to a point at which said distal cutter edges contact said receiver block and at which point said open ligating clips are closed.

2. A surgical instrument as defined in claim 1 in which said rod includes a knob attached to the distal end thereof.

3. A surgical instrument as defined in claim 1 in which said module includes spring means for biasing said movable jaw to an open position.

4. A surgical instrument as defined in claim 1 in which said cutting block includes a roughened surface between said pair of cutting blades.

5. A surgical instrument as defined in claim 1 in which said fixed jaw includes a hook-like guide extending therefrom.

6. A disposable surgical instrument for applying a pair of spaced apart ligating clips onto a tubular vessel and excising a segment of the vessel therebetween comprising:
    a disposable cutter and ligating clip module having a pair of spaced apart blocks, a first one of said pair of blocks having a pair of spaced apart cutting blades and a second one of said pair of blocks opposing said first block and having a cutting blade receiving surface, said blocks having grooves for holding a pair of spaced apart open ligating clips;
    spacing means for spacing said first and second block apart including a pair of pins having proximal ends thereof anchored to said second block and extending between said second block and said first block, said pins having distal ends frictionally engaging said first block, said friction to be overcome by pressure tending to move said first block toward said second block;
    a pair of open ligating clips disposed in said grooves; and
    handle means having a pair of open closable jaws for holding said module, said handle means including closing means for closing said jaws when a tubular vessel is disposed within said open clips and between said cutting blades and said receiving block, thereby clamping said pair of clips onto the tubular vessel and excising a segment thereof between said clips.

7. A surgical instrument as defined in claim 6 in which said distal ends of said pins includes first detents and said first block includes openings for receiving said distal ends and second detents engaging said first detents to provide said frictional engagement.

8. A surgical instrument as defined in claim 6 in which said clip module further includes compression spring means disposed between said pair of blocks for biasing said blocks toward an open position 9. A surgical instrument as defined in claim 6 in which said first and second blocks are formed of plastic.

10. A surgical instrument as defined in claim 6 in which said handle means is formed essentially of plastic.

* * * * *